United States Patent [19]

Clifford et al.

[11] Patent Number: 5,037,759
[45] Date of Patent: Aug. 6, 1991

[54] PROCESS FOR THE PREPARATION OF SUBSTITUTED PHENOXY PROPANOIC ACIDS

[75] Inventors: Kenneth H. Clifford; Gareth T. Phillips, both of Sittingbourne, England; Arthur F. Marx, Delft, Netherlands

[73] Assignees: Shell Internationale Research Maatschappij B.V., The Hague; Gist-Brocades NV, Delft, both of Netherlands

[21] Appl. No.: 277,929

[22] Filed: Nov. 30, 1988

[30] Foreign Application Priority Data

Dec. 1, 1987 [GB] United Kingdom ............... 8728064

[51] Int. Cl.$^5$ ................................................. C12P 7/40
[52] U.S. Cl. .................................... 435/280; 435/136; 435/141
[58] Field of Search ................... 435/280, 141, 136

[56] References Cited

U.S. PATENT DOCUMENTS 4,568,641 2/1986 Bewick ........................... 435/280
4,933,290 6/1990 Cesti et al. ..................... 435/280
4,943,528 7/1990 Nakamura et al. ............. 435/280

Primary Examiner—Sam Rosen

[57] ABSTRACT

The R-enantiomer of a compound of formula I:

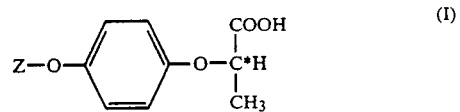

where Z is an optionally substituted cyclic organic moiety and C* represents an optically active carbon atom, may be prepared by supplying a substrate of formula II

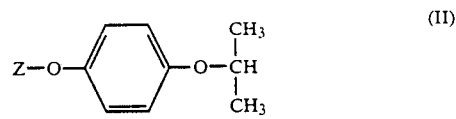

to a culture of a microorganism capable of oxidation of compound II into the R-enantiomer of I.

9 Claims, No Drawings

PROCESS FOR THE PREPARATION OF SUBSTITUTED PHENOXY PROPANOIC ACIDS

The present invention relates to a microbial process for the preparation of optically active substituted phenoxy propanoic acids, to novel substrates for the microbial process and to the preparation of such substrates.

The invention is particularly, but not exclusively, directed to the preparation of optically active herbicidal compounds of the class known as "PPP" herbicides in which phenoxy propanoic acid is substituted at the 4-position by a group —O—Z where Z is an optionally substituted phenyl group or alternatively an optionally substituted ring system such as naphthalene, pyridine, benzimidazole, benzoxazole, and benzothiazole. Such compounds have been found to have high selectivity towards monocotyledonous weeds such as wild oats, millet and blackgrass. Examples of such herbicides are described in a review article by H. J. Nestler in "Chemie de Pflanzenschutz und Schadlingsbekampfungsmittel, Vol. 8, p. 2 to 25, published by Springer-Verlag, Berlin. Such molecules exhibit chirality at $C_2$ of the propanoic acid moiety. It has been demonstrated that only one stereoisomer, the R-enantiomer, contributes the herbicidal activity when the herbicide is used in post emergence applications.

There is therefore a need to provide a preparative route for such herbicides in an enantiomerically pure form, especially for preparation of the R-enantiomer. The provision of substantially pure R-enantiomer allows the use of a decreased amount of product to produce the same herbicidal effect. However, previously proposed routes to this type of herbicide have not been entirely satisfactory in producing the desired R-enantiomer. Thus for routes which rely on the condensation of a monoalkylated hydroquinone with a compound providing the group Z, there are difficulties in preparing the starting material and in racemisation of the optically active centre. On the other hand routes which rely on the introduction of the optically active grouping in the final step involve initial synthesis of a phenoxyphenol prior to condensation with a reagent such as a chloropropionate under basic conditions. This again leads to possible racemisation.

According to the present invention, we provide a process for the preparation of a compound of formula I which is predominantly present as the R-enantiomer:

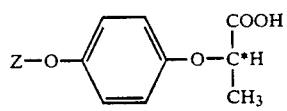

where Z is an optionally substituted cyclic organic moiety and C* represents an optically active carbon atom, comprising supplying a substrate of formula II

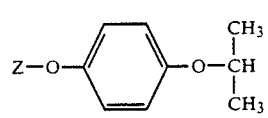

where Z is as defined above, to a culture of a microorganism capable of oxidation of a compound of formula II into predominantly the R-enantiomer of a compound of formula I, separating the compound of formula I from the culture medium and optionally converting the compound of formula I to an ester or salt thereof. Preferably the compound of formula I comprises at least 70%, more preferably at least 95%, by weight of the R-enantiomer.

The moiety Z may suitably be an optionally substituted aromatic or aliphatic carbocyclic group or a heterocyclic group. Such a group may be mono- or polycyclic. Preferred groups are optionally substituted phenyl groups and pyridyl groups. Examples of such groups are unsubstituted phenyl, halogen substituted phenyl such as 2,4-dichlorophenyl and substituted pyridyl, such as 5-trifluoromethyl-2-pyridyl optionally substituted at the 3-position by a halogen, e.g. a chlorine atom. Preferred substrates for the process of the invention are 2-(4-phenoxyphenoxy)propane, 2-[4-(2,4-dichlorophenoxy)-phenoxy]propane and 2-[4-(5-trifluoromethyl-2-pyridyloxy)-phenoxy]propane.

As the substrates of formula II are not optically active, they may be derived by a variety of routes. One process for the preparation of compounds of formula II comprises reacting a compound of formula III

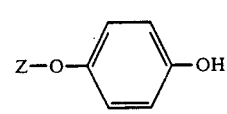

where Z is a group as defined above with a compound of formula

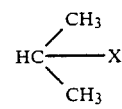

where X is a suitable leaving group, such as a sulphonate. The starting phenoxy phenol of formula III may be prepared by conventional synthetic methods.

Alternatively, and preferably, the compounds of formula II are prepared by reacting a compound of formula Z-A with a compound of formula IV

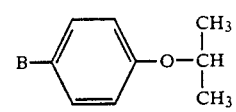

where Z is a group as defined above, one of A and B represents a hydroxy group and the other of A and B represents a leaving group, such as a halogen atom.

Certain compounds of formula II are novel. The novel compounds of formula II include compounds of formula IIa

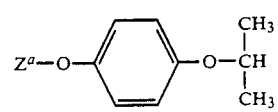

in which $Z^a$ represents a phenyl group or a 5-trifluoromethyl-2-pyridyl group optionally substituted at the 3-position by a halogen atom.

The compounds of formula IIa constitute a further aspect of the present invention.

The microorganism employed in the process of the invention may be any microorganism which is capable of oxidation of the substrate II into the R-enantiomer of compound I. Suitable microorganisms include bacteria belonging to the genera Rhodococcus, Nocardia and Pseudomonas, including cultures of the following species:

*Rhodococcus rhodochrous* (examples of this species are deposited in the NCIB under the accession numbers 12566, 11273 and 11277);

*Nocardia corallina* (an example of this species is deposited in the ATCC under the accession number 31338);

*Rhodococcus erythropolis* (an example of this species is deposited in the NCIB under the accession number 12574).

Variants and mutants of these bacteria, such as those produced by ultraviolet light or by chemical means may also be suitable.

Preferred microorganisms are *Rhodococcus rhodochrous*, especially that deposited under NCIB accession number 12566 and *Rhodococcus erythropolis*, especially that deposited under NCIB accession number 12574. These microorganisms have the following characteristics: *Rhodococcus rhodochrous* NCIB 12566

Single cell, nutrient agar medium, pH 7.3, 25° C.

| | |
|---|---|
| Shape: | Short rods |
| Axis: | Straight |
| Regularity: | Pleomorph/Club/Branched |

Colony, nutrient agar medium, pH 7.3, 37° C.

| | |
|---|---|
| Shape: | Circular |
| Elevation: | Convex |
| Colour: | Beige (Pink at 25° C.) |
| Opacity: | Opaque |
| Surface: | Shiny |
| Edge: | Entire |

*Rhodococcus erythropolis* NCIB 12574
Single cell, nutrient agar medium, pH 7.3, 30° C.

| | |
|---|---|
| Shape: | Stout rods |
| Regularity: | Pleomorphic |
| Sides: | Parallel/slightly irregular |

Colony, nutrient agar medium, pH 7.3, 30° C.

| | |
|---|---|
| Shape: | Circular |
| Elevation: | Flat |
| Texture: | Rough |
| Colour: | Pink |
| Opacity: | Opaque |
| Edge: | Crenated |

The selected microorganism is preferably cultured prior to exposure to the substrate, for example for about 0.5 to 10 days, whereafter the cells are suspended in a liquid salt medium, and the substrate then subjected to the action of the cells.

After the above mentioned cultivation for about 0.5 to 10 days the cells may be isolated from the culturing medium before suspending the cells in the minimal liquid nutrient medium. To grow the micro-organisms used for the oxidation, ordinary culture mediums containing an assimilable carbon source (for example glucose, lactate, hydrocarbons like tetradecane (C14), etc.), a nitrogen source (for example ammonium sulphate, ammonium nitrate, ammonium chloride, etc.), with an agent for an organic nutrient source (for example yeast extract, malt extract, peptone, meat extract, etc.) and an inorganic nutrient source (for example phosphate, magnesium, potassium, zinc, iron and other metals in trace amounts) may be used. Optionally an inducer (for example diethoxymethane) is added to the culture medium. A temperature between 0° and 45° C. and a pH between 3.5 and 9 is maintained during the growth of the micro-organisms. Preferably the micro-organisms are grown at a temperature between 20° and 37° C. and at a pH between 5 and 8.

The aerobic conditions required during the growth of the micro-organisms can be provided according to any of the well established procedures, provided that the supply of oxygen is sufficient to meet the metabolic requirement of the micro-organisms. This is most conveniently achieved by supplying gaseous oxygen, preferably in the form of air.

During the conversion of compound II into compound I the microorganisms may be in a growing stage using an above mentioned ordinary culture medium. The microorganisms may be supplemented with a cosubstrate.

However, preferably during the conversion of compound II into compound I the microorganisms are held in a substantially non-growing stage using a minimal culture medium. As minimal culture medium, an ordinary culture medium may be used containing an assimilable carbon source when required (for example glucose, lactate, hydrocarbons like tetradecane (C14), etc.) a nitrogen source when required (for example ammonium sulphate, ammonium, nitrate, ammonium chloride, etc.), with an agent for an organic nutrient source when required (for example yeast extract, malt extract, peptone, meat extract, etc.) and an inorganic nutrient source when required (for example phosphate, magnesium, potassium, zinc, iron and other metals in trace amounts). The micro-organisms can be kept in the non-growing stage for example under exclusion of the assimilable carbon source or under exclusion of the nitrogen source. A temperature between 0° and 45° C. and a pH between 3.5 and 9 is maintained during this stage. Preferably the microorganisms are kept at a temperature between 20° and 37° C. and a pH between 5 and 8. The aerobic conditions required during this stage can be provided according to the abovementioned procedures, provided that the supply of oxygen is sufficient to meet the metabolic requirement of the microorganisms but also to effect the desired oxidation. The product produced by the micro-organisms as mentioned above, can be recovered and purified according to any of the well established procedures. Compounds of formula I can be converted into esters or salts by established procedures if desired.

The invention will now be further described with reference to the following examples.

Analytical Methods

High Pressure Liquid Chromatography (HPLC)

Analyses of products from incubations were carried out by HPLC. Incubations were acidified with 5N sulphuric acid and extracted twice with an equal volume of dichloromethane. The solvent extracts were then combined and evaporated to dryness; the solid residues were dissolved in an appropriate volume of HPLC solvent and analysed by HPLC.

Conditions for the HPLC were as follows: a reverse-phase column, Lichrosorb RP18, 10 micron, 125×4.9 mm was used with a $2\times10^{-2}$ ml injection loop on a Rheodyne injection valve. The solvent used throughout was 70-30 v/v acetonitrile - 2% acetic acid at a flow rate of 1 ml min$^{-1}$ and detection was achieved with an ultra-violet monitor set at $280\times10^{-9}$ m.

Preparative HPLC

To purify samples for further analysis the analytical HPLC described above was used with only one modification: the injection loop was replaced with a $2\times10^{-1}$ ml loop. After repeated injections of $2\times10^{-1}$ ml, samples were collected, combined and evaporated to dryness.

Chiral HPLC

All samples were analysed for enantiomeric composition as their methyl esters. Methanolic solutions of samples (1-5 mg) were transferred to capped vials, the methanol being evaporated and 0.5 ml "Methyl-8" (Pierce & Warriner) reagent (dimethylformamide dimethylacetal (2 mEq/ml in pyridine)) added. The samples were heated to 60° C. for 10 min after which the solvent was evaporated and the samples were then dissolved in minimal quantities of HPLC solvent (0.1-0.5 ml).

Chromatography was performed on a column of immobilised D-phenylglycine: 250×4.9 mm (I.D.) column containing CHI-PGC-250A (D-3,5-dinitrobenzoylphenylglycine bonded silica (5 m) (supplied by Hichrom Ltd., Reading).

Polarimetry

Optical rotations were determined using a Perkin Elmer Polarimeter model 241 in a cell 0.1 m light-path at $=589\times10^{-9}$ m and maintained at 20° C.

Nuclear Magnetic Resonance ($^1$H-nmr)

Deuterated chloroform was used as the solvent for all samples.

Mass Spectrometry (ms)

All mass spectral analyses were performed using both chemical ionisation, with methane as the reagent gas, and electron impact ionisation.

Growth Media

| Ammonium salts medium (ASM) Composition | g/liter |
|---|---|
| Ammonium chloride | 0.535 |
| Potassium dihydrogenphosphate | 0.531 |
| Disodium hydrogenphosphate | 0.866 |
| Potassium sulphate | 0.174 |
| Magnesium sulphate.7H$_2$O | 0.037 |
| Calcium chloride.2H$_2$O | 0.00733 |
| TK3 trace element solution | 0.1 ml |
| Ferrous sulphate.7H$_2$O (added after autoclaving) | 0.0189 |
| pH adjusted to 7.0 | |
| Phosphate medium (PSX) composition | g/liter |
| Potassium dihydrogen phosphate | 8.92 |
| Disodium hydrogen phosphate | 2.84 |
| Diammonium hydrogen phosphate | 1.0 |
| Ammonium sulphate | 0.2 |
| Potassium chloride | 0.2 |
| Trisodium citrate | 0.294 |
| Calcium sulphate.2H$_2$O | 0.005 |
| Magnesium sulphate.7H$_2$O | 0.2 |
| PS2 T/E | 10.0 |
| TK3 trace element solution | |
| ZnSO$_4$.7H$_2$O | 0.288 g |
| MnSO$_4$.4H$_2$O | 0.224 g |
| H$_3$BO$_3$ | 0.0618 g |
| CuSO$_4$.5H$_2$O | 0.1248 g |
| Na$_2$MoO$_4$.2H$_2$O | 0.0484 g |
| CoCl$_2$.6H$_2$O | 0.0476 g |
| KI | 0.083 g |
| 1N H$_2$SO$_4$ | 1 ml |
| Dissolved in 1 liter distilled water | |
| PS2 T/E | |
| (NH$_4$)$_2$SO$_4$.FeSO$_4$.6H$_2$O | 0.25 g |
| ZnSO$_4$.7H$_2$O | 0.05 g |
| MnCl$_2$.4H$_2$O | 0.03 g |
| CuSO$_4$.5H$_2$O | 0.015 g |
| CoCl$_2$.6H$_2$O | 0.015 g |
| H$_3$BO$_3$ | 0.005 g |
| Na$_2$MoO$_4$.H$_2$O | 0.0055 g |
| KI | 0.01 g |
| Dissolved in 1 liter distilled water | |

EXAMPLE 1

Growth of *Rhodococcus rhodochrous* NCIB 12566

*Rhodococcus rhodochrous* NCIB 12566 was grown in 100 ml phosphate medium PSX described above with n-heptane from a centre-well for 5 days at 30° C. on a shaker. The resulting medium was used to inoculate 1,600 ml. PSX medium in 4×2000 ml flasks with n-heptane in centre wells. These flasks were incubated for 5 days at 30° C. on a shaker at 200 rpm. The cells were collected by centrifugation and washed with an equal volume of ASM medium described above. The cells were finally suspended in ASM (200 ml) prior to addition of substrate.

EXAMPLE 2

Growth of *Rhodococcus erythropolis* NCIB 12574

*Rhodococcus erythropolis* NCIB 12574 was grown in 3×100 ml phosphate medium PSX described above with 0.5 ml tetradecane for four days at 30° C. on a shaker. The cells were gathered by centrifugation and suspended in 30 ml ASM medium (dry weight 10.3 mg ml$^{-1}$) prior to addition of substrate.

EXAMPLE 3

Preparation of (R)-(+)-2-(4-phenoxyphenoxy)propanoic acid

To a suspension of *R. rhodochrous* NCIB 12566 in ASM medium (200 ml) prepared as described in Example 1, was added as substrate 2-(4-phenoxyphenoxy)propane (100 mg) in dimethyl formamide (1 ml).

The suspension was incubated for 5 days at 30° C. on a shaker at 200 rpm and the incubation was acidified with 5N sulphuric acid (5 ml) and extracted twice with an equal volume of dichloromethane. The extracts were dried over anhydrous sodium sulphate and evaporated to dryness. The residues were extracted with 4×5 ml. HPLC solvent (70-30 acetonitrile - 2% acetic acid) and the extracts evaporated overnight with a stream of nitrogen. The residues were again dissolved in HPLC solvent (1 ml) and purified by preparation HPLC as described above.

The products were analysed by 'H-nmr, ms, polarimetry and chiral HPLC as described above. The major product was shown to be R-(+)-2-(4-phenoxyphenoxy)propanoic acid (39% yield; 117 mg $l^{-1}$) while the minor product was 2-[4-hydroxy phenoxyphenoxy] propane (20% yield; 60 mg $l^{-1}$).

R-(+)-2-(4-phenoxyphenoxy)propanoic acid gave a mass spectrum with the parent ion at m/z=259 (m+1) with a fragment at m/z=213 corresponding to the decarboxylated ion and a fragment at m/z=187 corresponding to the protonated 4-phenoxyphenol.

The 'H nmr spectrum of the major compound R-(+)-2-(4-phenoxyphenoxy)propanoic acid showed:

$\delta$H (360 Mhz; CDCl$_3$ solvent; standard Me$_4$Si) 1.68 (3H, d, CH$_3$); 4.74 (1H, q, O—C—H); 6.9 (2H, d, $c^{2,6}$); 6.98 (4H, ABq, $c^{2',3',5',6'}$); 7.07 (1H, t, C$^4$); 7.32 (2H, q, C$^{3,5}$)

Chiral HPLC of the methyl ester of the major product showed that the product was more than 99% R-enantiomer. Chirality was confirmed by polarimetry which gave $[\alpha]_D^{20} = +26°$ (C 0.084 in methanol).

EXAMPLE 4

Preparation of (R)-(+)-2-[4-(2,4-dichlorophenoxy)phenoxy]-propanoic acid

Example 3 was repeated using as substrate 2-[4-(2,4-dichlorophenoxy)phenoxy]propane.

Analysis of the products showed the presence of the title compound (3.4% yield, 17 mg $l^{-1}$) and 2-[4-(hydroxy)-2,4- dichlorophenoxy)phenoxy]propane.

After purification by preparative HPLC R-(+)-2-[4-(2,4-dichloro- phenoxy)-phenoxy]propanoic acid was methylated and the methyl ester used for chiral and structural analysis. Analysis of this methyl ester by chiral HPLC showed that it was essentially 100% R-2-[4-(2,4-dichlorophenoxy)-phenoxy]propanoic acid, methyl ester.

This methyl ester was then subject to analysis by chemical ionisation mass spectrometry; the double isotope effect of chlorine can be seen in several ions. The m/z=341 corresponds to the parent ion; m/z=281 corresponds to the decarboxylated ion, the ion m/z=255 corresponds to the dichlorophenoxy phenol ion and the ion m/z=196 corresponds to the phenoxy propanoate, methyl ester fragment.

The 'Hnmr spectrum of the methyl ester of the title compound showed $\delta$H (360 MHz; CDCl$_3$ solvent; standard Me$_4$Si) 1.62 (3H, d, CH$_3$); 3.77 (3H, s, COOCH$_3$); 4.72 (1H, q, O—CH); 6.8 (1H, d, C$^6$); 6.88 (4H, ABq, $C^{2',3',5',6'}$); 7.15 (1H, dd, C$^5$); 7.45 (1H, s, C$^3$)

EXAMPLE 5

Preparation of R-(+)-2-[4-(5-trifluoromethyl-2-pyridyloxy)phenoxy]-propanoic acid Example 3 was repeated using as substrate 2-[4-(5-trifluoromethyl-2-pyridyloxy)phenoxy]propane. The incubation gave only one product. This proved to be R-(+)-2-[4-(5-trifluoromethyl-2-pyridyloxy)-phenoxy]-propanoic acid in high yield (57% yield, 285 mg $l^{-1}$). After purification and methylation, chiral HPLC showed the enantiomeric purity of this product to be approximately 98%.

The 'Hnmr spectrum of the title compound showed $\delta$H (360 MH$_2$; CDCl$_3$ solvent; standard Me$_4$Si) 1.68 (3H, d, CH$_3$); 4.78 (1H, q, O—C—H); 6.93 (1H, d, C$^3$); 7.03 (4H, ABq, $C^{2',3',5',6'}$); 7.88 (1H, dd, C$^4$); 8.4 (1H, bv.s., C$^6$)

EXAMPLE 6

Preparation of R-(+)-2-[4-(5-trifluoromethyl-2-pyridyloxy)-phenoxy]-propanoic acid To a suspension of cells of R. erythropolis NCIB 12574, prepared as described in Example 2 was added 30 mg of 2-[4-(5-trifluoromethyl-2-pyridyloxy)-phenoxy]propane. The incubation gave only one product, which proved to be the title compound (35% yield, 355 mg.$l^{-1}$) which was purified and identified as in Example 5.

EXAMPLE 7

Preparation of 2-(4-phenoxyphenoxy)propane

Sodium hydride (3.0 g, 0.125 mole) was added in portions to a stirred mixture of 20 g (0.107 mole) of 4-phenoxyphenol and 90 ml of dry N,N-dimethylformamide. After the hydrogen evolution had stopped 17 g (0.123 mole) of the methylsulphonate of 2-propanol were added and stirring was continued at 50°-60° C. for 3 hours.

More sulphonate (1 ml) and sodium hydride (0.3 g) were added and after stirring for 1 hour at 70° C. the mixture was cooled and poured into 0.9 liter of cold water.

The precipitate was filtered off, washed with water and crystallised from 120 ml of hot methanol (filtered hot) to give 19.91 g of pure title compound.

'H nmr ($\delta$, CDCl$_3$, 360 MHz, Me$_4$Si) 1.68 (6H, d, CH$_3$); 4.7 (1H, sept, O—C—H); 6.9 (2H, d, C$^{2,6}$); 6.98 (4H, ABq, $C^{2',3',5',6'}$); 7.10 (1H, t, C$^4$); 7.32 (2H, q, C$^{3,5}$)

EXAMPLE 8

Preparation of 2-[4-(2,4-dichlorophenoxy)phenoxy]-propane a) 2-[4-(2,4-dichlorophenoxy)phenoxy]-propanol-1

A solution of 34.1 g (0.1 mole) of (R,S)-methyl-2-[4-(2,4-dichlorophenoxy)-phenoxy]propionate in 100 ml of dry ether was added dropwise over a period of 25 minutes to a stirred and refluxing suspension of 5 g (0.13 mole) of lithium aluminium hydride in 100 ml of dry ether. Stirring was continued for 10 minutes at 20° C. and next 5 ml of water were added dropwise followed by 5 ml of 15% w/v of sodium hydroxide and 15 ml of water. After stirring for half an hour the granulate was filtered, washed with ether and the filtrate was dried with magnesium sulphate, filtered and evaporated to give 28.33 g of crude title compound as an oil.

b) 1-(4-toluenesulphonyloxy)-2-[4-(2,4-dichlorophenoxy)phenoxy] propane.

A mixture of 27.78 g (88.7 mmole) of 2-[4-(2,4-dichlorophenoxy)phenoxy]propanol-1, 150 ml of dry pyridine and 22.5 g (118 mmole) of 4-toluene sulphonyl chloride was stirred for 20 hours at 20° C.

The mixture was poured into half a liter of cold water and extracted with ether (2×). The extract was washed with excess 5% hydrochloric acid, water, 1M sodium bicarbonate and brine respectively, dried with anhydrous magnesium sulphate, filtered and evaporated to give 39.59 g of product.

c) 2-[4-(2,4-dichlorophenoxy)phenoxy]propane

A suspension of 32 g (68.5 mmole) of 1-(4-toluene sulphonyloxy)-2-[4-(2,4-dichlorophenxoy)phenoxy]- propane, 300 ml of dry ether and 4 grams (105 mmole) of lithium aluminium hydride was stirred at 20° C. for 8 hours. Next 4 ml of water were added dropwise followed by 4 ml of 15% w/v sodium hydroxide and 16 ml of water with intermittent stirring. The granulate was filtered, washed with ether and the filtrate was dried with magnesium sulphate, filtered and evaporated to give 19.78 g of oil. This was chromatographed over 200 g of silica gel with ether/hexane=1/9 in 50 ml fractions. The fractions 6, 7 and 8 were combined and evaporated to dryness to give 17.0 g of title compound as a mobile oil.

$^1$H nmr ($\delta$, CDCl$_3$, 360 MHz, Me$_4$Si) 1.62 (6H, d, CH$_3$); 4.72 (1H, sept, O—C—H); 6.8 (H, d, C$^6$); 6.88 (4H, ABq, C$^{2',3',5',6'}$); 7.15 (1H, dd, C$^5$); 7.45 (1H, s, C$^3$)

EXAMPLE 9

Preparation of 2-[4-(5-trifluoromethyl-2-pyridyloxy)-phenoxy]propane

Sodium hydride (3.7 g, 0.154 mole) was added in portions to a stirred mixture of dry N,N-dimethylformamide (60 ml) and 4-isopropyloxyphenol (26 g, 0.17 mole). After hydrogen evolution had stopped, 2-chloro-5-trifluoromethylpyridine (28.75 g, 0.158 mole) was added and stirring was continued for 1.75 hours at 80°-95° C. Further sodium hydride (0.4 g) was added. After stirring for 1.25 hours at 95° C., the mixture was cooled and poured into water. The water was extracted twice with toluene, the extracts washed with 1M sodium hydrogen carbonate and brine, filtered and evaporated to a brown oily residue which was purified over silica gel with 1:9 ether/hexane as eluant to give the title compound (37.34 g).

$^1$H nmr ($\delta$, CDCl$_3$, 360 MHz, Me$_4$Si) 1.7 (6H, d, CH$_3$); 4.78 (1H, sept, O—C—H); 6.93 (1H, d, C$^3$); 7.03 (4H, ABq, C$^{2',3',5',6'}$); 7.88 (1H, dd, C$^4$); 8.4 (1H, br.s., C$^6$).

We claim:

1. A process for the preparation of a compound of formula I which is predominantly present as the R-enantiomer:

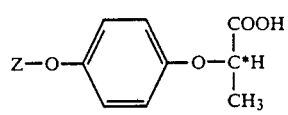

where Z is an optionally substituted cyclic organic moiety and C* represents an optically active carbon atom, comprising supplying a substrate of formula II

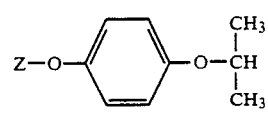

where Z is as defined above, to a culture of a microorganism capable of oxidation of a compound of formula II into predominantly the R-enantiomer of a compound of formula I, separating the compound of formula I from the culture medium and optionally converting the compound of formula I to an ester or salt thereof.

2. A process according to claim 1, wherein the compound of formula I comprises at least 70% by weight of the R-enantiomer.

3. A process according to claim 2, wherein the compound of formula I comprises at least 95% by weight of the R-enantiomer.

4. A process according to claim 1, 2 or 3 wherein Z is an optionally substituted aromatic or aliphatic carbocyclic group or a heterocyclic group.

5. A process according to claim 4 wherein Z represents a phenyl group, a halogen substituted phenyl group or a substituted pyridyl group.

6. A process according to any claim 1 wherein the microorganism is a bacterium of the genus Rhodococcus, Nocardia or Pseudomonas.

7. A process according to claim 6 wherein the microorganism is selected from *Rhodococcus rhodochrous, Nocardia corallina,* or *Rhodococcus erythropolis.*

8. A process according to claim 7 wherein the microorganism is *Rhodococcus rhodochrous* NCIB 12566 or *Rhodococcus erythropolis* NCIB 9158 or a variant or mutant thereof.

9. A process according to claim 1 wherein the microorganism is cultured prior to exposure to the substrate and, during exposure to the substrate, the microorganism is held in a substantially non-growing stage under aerobic conditions.

* * * * *